(12) United States Patent
Zhavoronkov et al.

(10) Patent No.: US 9,642,574 B2
(45) Date of Patent: May 9, 2017

(54) BIOMETRIC SENSORS ASSEMBLY FOR A HARD HAT

(71) Applicants: Mikhail Zhavoronkov, Northville, MI (US); Gerrit Reepmeyer, Novi, MI (US); Saikat Dey, Birmingham, MI (US)

(72) Inventors: Mikhail Zhavoronkov, Northville, MI (US); Gerrit Reepmeyer, Novi, MI (US); Saikat Dey, Birmingham, MI (US)

(73) Assignee: GuardHat, Inc., Southfield, MI (US)

( * ) Notice: Subject to any disclaimer, the term of this patent is extended or adjusted under 35 U.S.C. 154(b) by 0 days.

(21) Appl. No.: 15/259,406

(22) Filed: Sep. 8, 2016

(65) Prior Publication Data

US 2017/0000417 A1    Jan. 5, 2017

Related U.S. Application Data

(60) Continuation-in-part of application No. 15/150,384, filed on May 9, 2016, which is a continuation-in-part of application No. 14/883,157, filed on Oct. 14, 2015, which is a division of application No. 14/590,596, filed on Jan. 6, 2015, now Pat. No. 9,177,458, which is a division of application No. 14/517,385, filed on Oct. 17, 2014, now Pat. No. 9,013,297.

(51) Int. Cl.
| | |
|---|---|
| *G08B 23/00* | (2006.01) |
| *A61B 5/00* | (2006.01) |
| *G08B 21/02* | (2006.01) |
| *H04Q 9/00* | (2006.01) |
| *A42B 3/04* | (2006.01) |
| *G08B 21/04* | (2006.01) |

(52) U.S. Cl.
CPC ............ *A61B 5/6803* (2013.01); *A42B 3/046* (2013.01); *A61B 5/486* (2013.01); *A61B 5/7455* (2013.01); *G08B 21/02* (2013.01); *G08B 21/0453* (2013.01); *H04Q 9/00* (2013.01); *A61B 2503/20* (2013.01)

(58) Field of Classification Search
CPC ........ A61B 5/6803; A61B 5/486; A42B 3/324
USPC ............................. 340/573.1, 5.82, 4.12, 7.6
See application file for complete search history.

(56) References Cited

U.S. PATENT DOCUMENTS

| | | | |
|---|---|---|---|
| 4,665,385 A | 5/1987 | Henderson | |
| 6,798,392 B2 | 9/2004 | Hartwell et al. | |
| 6,992,580 B2 | 1/2006 | Kotzin et al. | |
| 7,110,743 B2 * | 9/2006 | Depew et al. | ........... A42B 3/30 381/375 |
| 7,188,767 B2 | 3/2007 | Penuela et al. | |

(Continued)

OTHER PUBLICATIONS

International Search Report and Written Opinion for Application No. PCT/US2015/020743 dated Jul. 31, 2015.

*Primary Examiner* — Toan N Pham
(74) *Attorney, Agent, or Firm* — Simonelli IP, PLLC

(57) ABSTRACT

A biometric sensor assembly measures biometric data of a wearer of a hardhat. The biometric sensor assembly includes a suspension harness to be removably secured to the hardhat. A biometric sensor is attached to the suspension harness in a way that allows direct or indirect contact with the wearer to enable measurement of the biometric data. The biometric sensor assembly also includes an electrical connection of the biometric sensor and the hardhat for data and power transmission.

6 Claims, 4 Drawing Sheets

(56) References Cited

U.S. PATENT DOCUMENTS

| | | | |
|---|---|---|---|
| 7,298,258 B1 * | 11/2007 | Hudgens et al. | F16P 3/14 340/3.1 |
| 7,570,170 B2 | 8/2009 | Wallner | |
| 7,592,911 B1 | 9/2009 | Hudgens et al. | |
| 7,830,249 B2 | 11/2010 | Dorneich et al. | |
| 8,040,292 B2 | 10/2011 | Ronzani et al. | |
| 8,446,273 B2 | 5/2013 | Humphrey et al. | |
| 8,671,467 B2 * | 3/2014 | Tack et al. | A42B 3/04 2/422 |
| 2005/0001728 A1 | 1/2005 | Appelt et al. | |
| 2008/0088434 A1 | 4/2008 | Frieder et al. | |
| 2009/0126059 A1 | 5/2009 | Tack et al. | |
| 2011/0115623 A1 | 5/2011 | Gnanasekaran et al. | |
| 2012/0304367 A1 * | 12/2012 | Howard et al. | A42B 3/046 2/413 |
| 2014/0240120 A1 | 8/2014 | Mao et al. | |
| 2015/0159846 A1 * | 6/2015 | Hollinger | H05B 33/0806 362/183 |

* cited by examiner

BIOMETRIC SENSORS ASSEMBLY FOR A HARD HAT

This is a continuation-in-part of U.S. patent application Ser. No. 15/150,384, filed May 9, 2016, which is a continuation-in-part of U.S. patent application Ser. No. 14/883,157, filed Oct. 14, 2015, which is a divisional of U.S. Pat. No. 9,177,458, which is a divisional of U.S. Pat. No. 9,013,297, which was filed on Oct. 17, 2014.

BACKGROUND ART

1. Field of the Invention

The invention relates generally to the field of wearable devices. More particularly, the invention relates to wearable devices having sensors, including biometric sensors, attached thereto.

2. Description of the Related Art

Helmets and other protectable wearables are often required when working in areas where there is a potential for injury. Helmets are especially required to protect the head from hazards such as impact from falling objects, scraping or bumping one's head on equipment, or contact with electrical conductors. Traditional suspension bands have been designed to extend inside the helmet and be used for spreading the helmet's weight and the force of any impact over the top of a user's head.

SUMMARY OF THE INVENTION

A biometric sensor assembly measures biometric data of a wearer of a hardhat. The biometric sensor assembly includes a suspension harness to be removably secured to the hardhat. A biometric sensor is attached to the suspension harness in a way that allows direct or indirect contact with the wearer to enable measurement of the biometric data. The biometric sensor assembly also includes an electrical connection of the biometric sensor and the hardhat for data and power transmission.

BRIEF DESCRIPTION OF THE DRAWINGS

Advantages of the invention will be readily appreciated as the same becomes better understood by reference to the following detailed description when considered in connection with the accompanying drawings, wherein.

DETAILED DESCRIPTION OF THE PREFERRED EMBODIMENT

Figure 1:
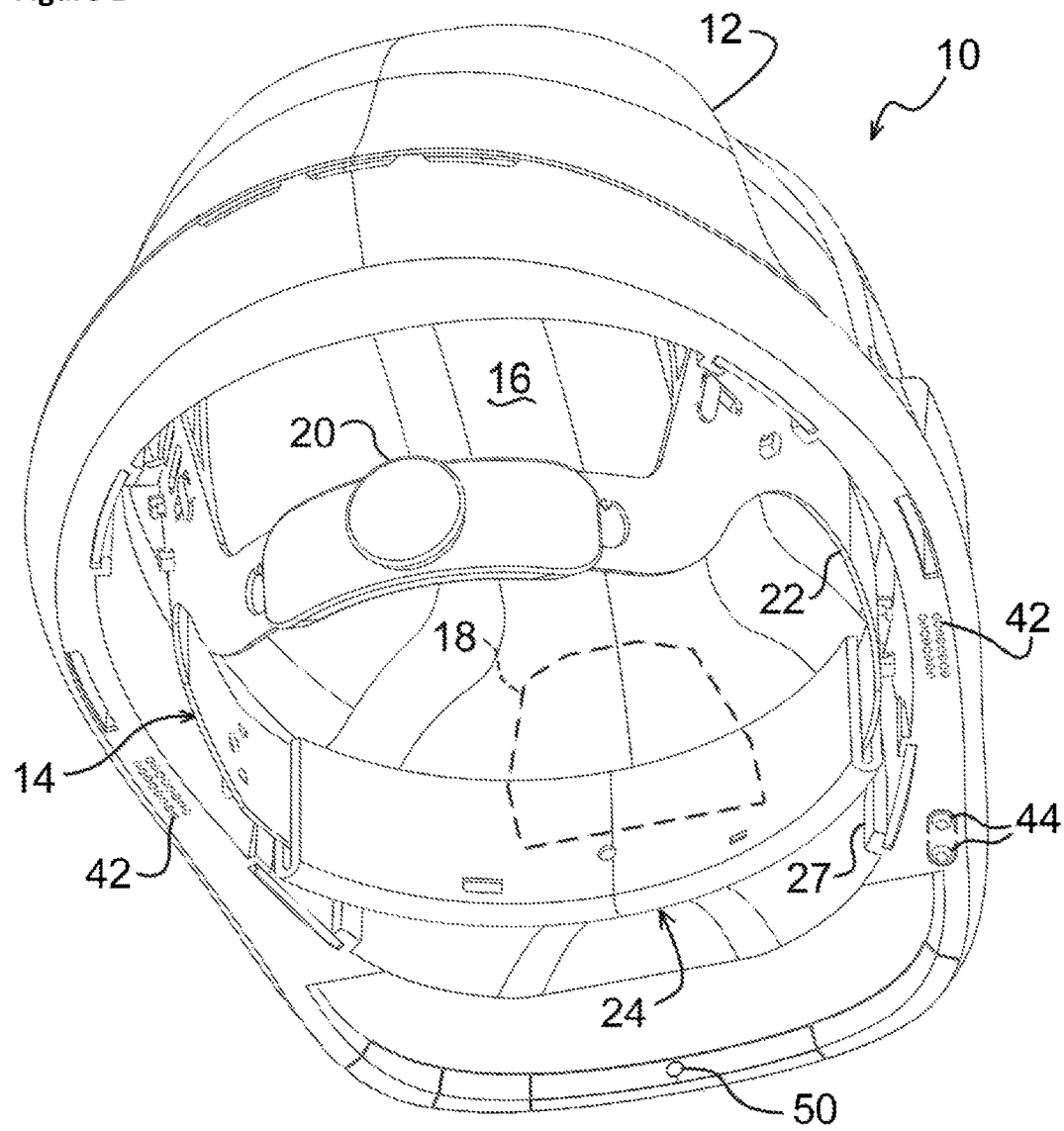
FIG. 1 is a perspective bottom view of the hard hat with electronics incorporated including the suspension band.

FIG. 1 illustrates a hard hat, generally shown at 10, including an outer shell 12 and an adjustable suspension band assembly, generally indicated at 14. The suspension band assembly 14 extends around the interior 16 of the hard hat 10. The adjustable suspension band assembly 14 allows the user to adjustingly secure the outer shell 12 to the user's and to absorb energy from impacts and collisions via a connecting clip structure 27 that connects the suspension band assembly 14 with the outer shell 12 of the hard hat 10.

The adjustable suspension band 14 includes an adjusting device 20 that adjusts the diameter of a primary support loop 22. The suspension band including its electrical connection are described in greater detail in a U.S. patent application Ser. No. 15/150,384, the disclosure of which is hereby incorporated by reference.

The hard hat 10 in FIG. 1 further includes a control unit 18 that may include electronic components and computing power to potentially enable electronic data processing capability locally within the hard hat 10. Also, the hard hat 10 may include a set of speakers 42 including corresponding volume buttons 44 to potentially enable audio communication within the hard hat 10 and a microphone (not shown) to capture audible signals/voices that are near the hard hat 10. In addition, the hard hat 10 could also include a light indicator 50 to provide visual feedback to the wearer.

The primary support loop 22 of the suspension band assembly 14 includes an electronic peripheral, which can take the form of a biometric sensors assembly 24 described in this patent in more detail later in FIGS. 3 and 4.

Figure 2:
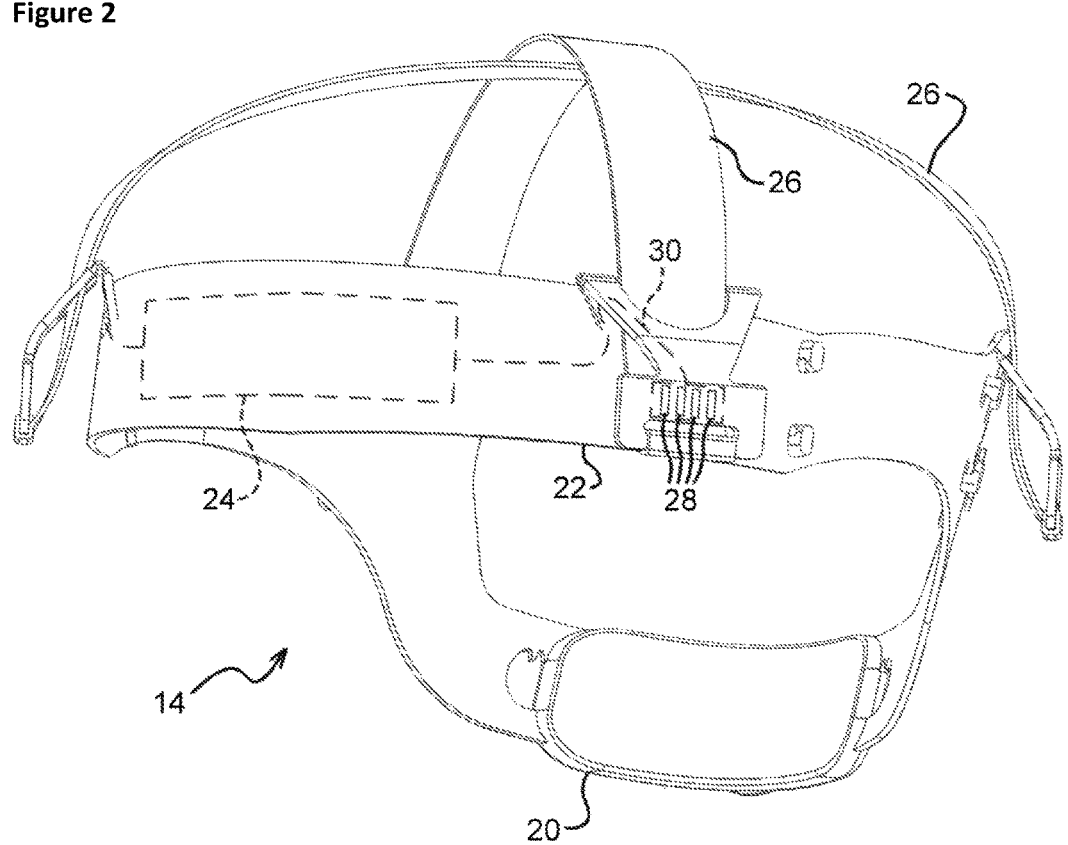
FIG. 2 is a perspective side view of the suspension band.

As shown in FIG. 2, the suspension band assembly 14 includes two attachment straps 26 that extend diametrically over the primary support loop 22 in a manner that provides enough slack to allow the head of the user to comfortably extend through the primary support loop 22. In some instances, the two attachment straps 26 may be adjustable to allow the user to have the two attachment straps 26 rest on the top of his or her head, providing more support and comfort.

An electrical anchor contact 28 is fixedly secured to the attachment strap 26 and provides an electrical connection between the hard hat 10 and the electronic peripheral as illustrated by the biometric sensors assembly 24 on the primary support loop 22. There may be more than one electrical anchor contact 28. Extending up from the electrical anchor contact 28 through the attachment strap 26 is an electrical conductor 30. The electrical conductor 30 completes the circuit between the biometric sensors assembly 24 in the primary support loop 22 and the control unit 18 that is attached to the outer shell 12 of the hard hat 10 (as shown in FIG. 1).

Figure 3:
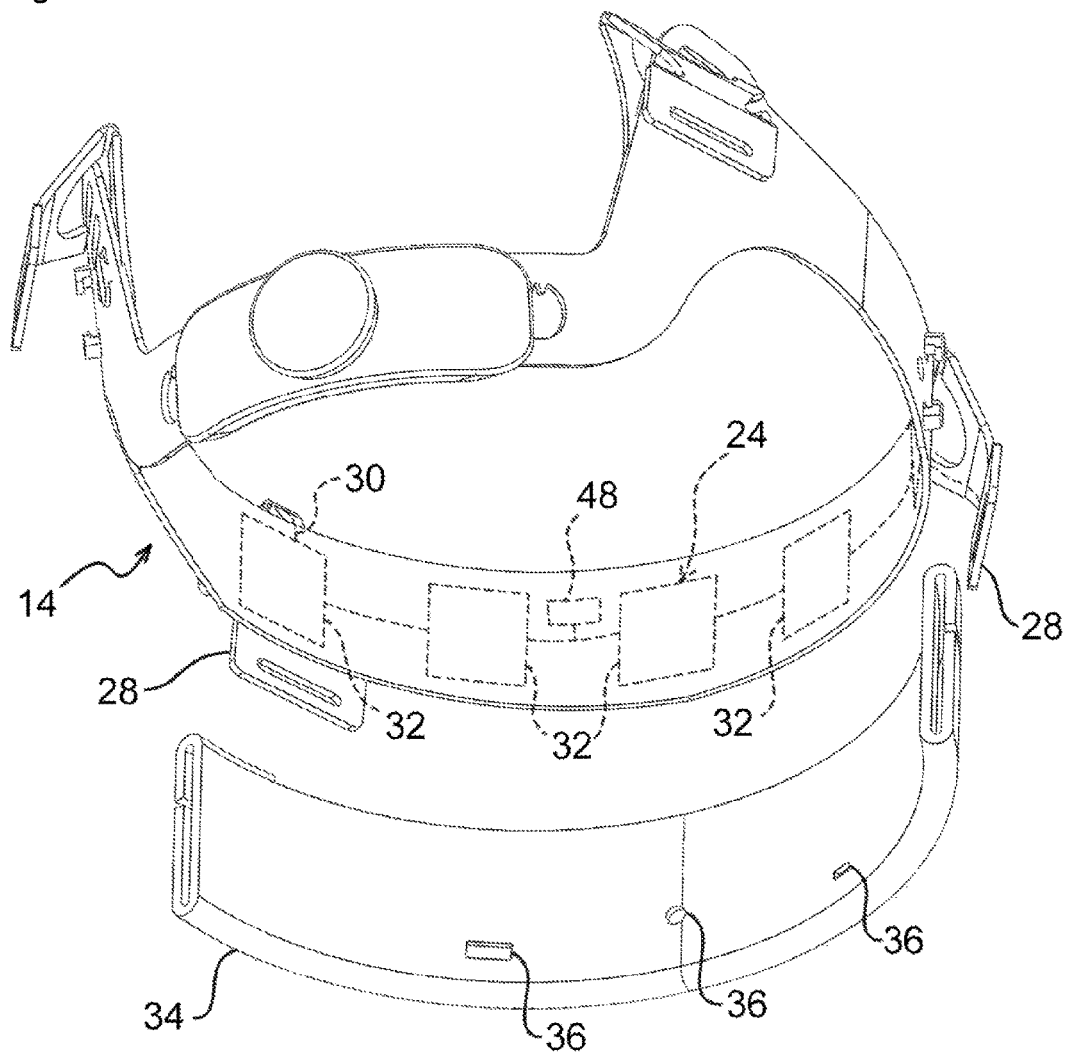
FIG. 3 is an exploded perspective view of the suspension band with sensors and a sweat band incorporated therein.

In FIG. 3, the setup of the biometric sensors assembly 24 is illustrated in more detail. As shown, the biometric sensors 32 are directly incorporated in the suspension band assembly 14. The biometric sensors 32 are electrically connected through the same electrical conductor 30 that connects the biometric sensors assembly 24 through the electrical anchor contact 28 with the control unit 18. This electrical connection ensures data and power transmission from the biometric sensors assembly 24 to the central control unit 18 and vice versa. The data connection will allow for processing the sensor data at the control unit 18.

The biometric sensors 32 can include any form of biometric sensor, such as for example, an optical heart rate monitor or a body temperature sensor. The suspension band assembly 14 might also include a haptic motor 48 to potentially provide haptic feedback to the wearer. The biometric sensors 32 and the haptic the motor 48 are usually covered by a cover or sweat band 34 that is placed over the suspension band assembly 14 and that encapsulates both the biometric sensors 32 and the haptic motor 48. The cover or sweat band 34 is forming the interface between the wearer's forehead and the biometric sensors 32 and/or the haptic motor 48. The cover or sweat band 34 should contain holes 36 at certain locations to allow the sensors to produce accurate sensor readings from the wearer's forehead. The cover or sweat band 34 is removable for cleaning purposes.

Figure 4:
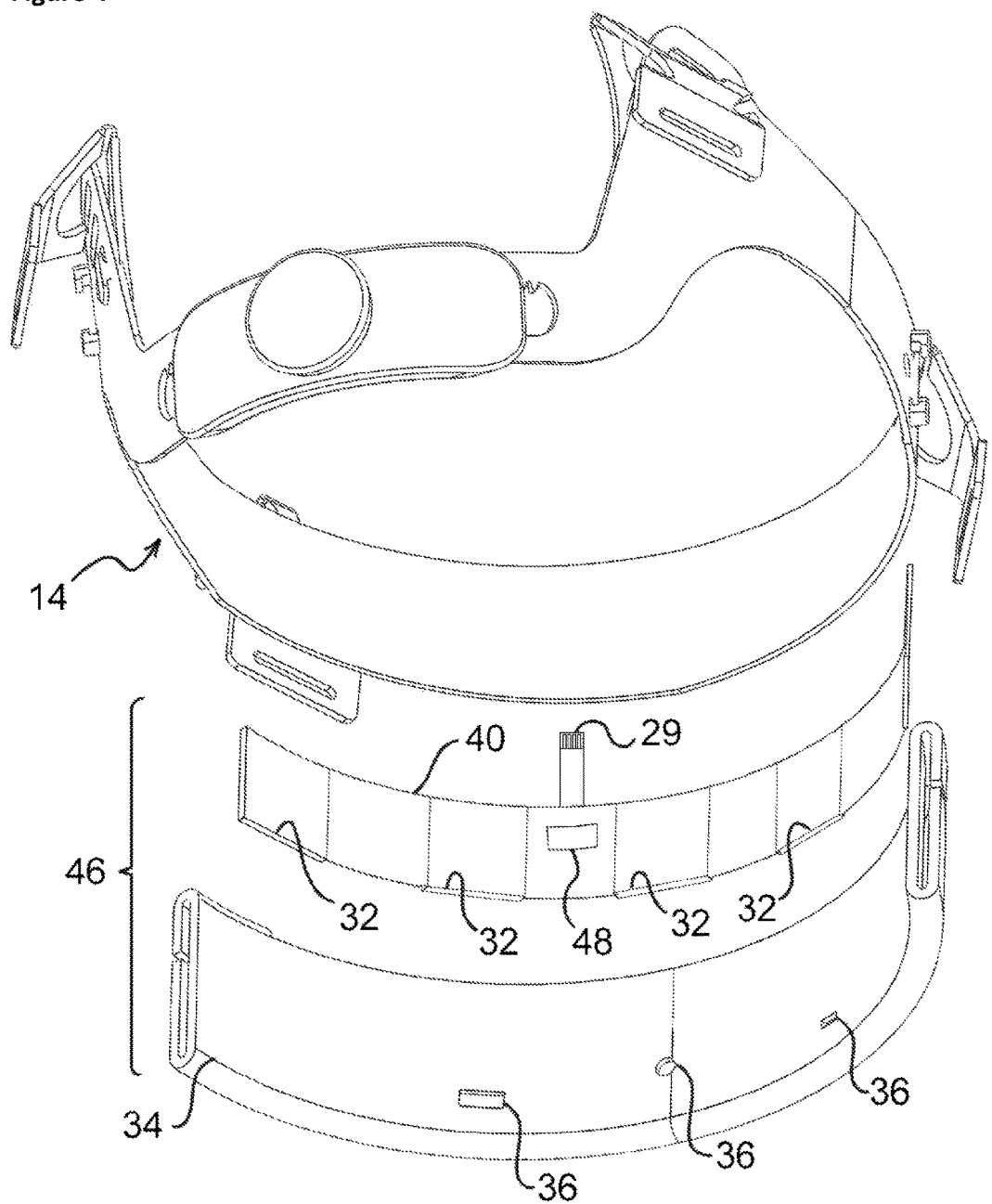
FIG. 4 is an exploded perspective view of an alternative embodiment of the invention.

An alternative to directly incorporating the biometric sensors 32 into the suspension band assembly 14 and then using a cover or sweat band 34 to protect the sensors would be to include the biometric sensors 32 directly into an integrative band 46, is illustrated in FIG. 4. The integrative band 46 represents one assembly unit that combines a conductive pad 40 and a sweat band 34. The biometric sensors 32 and potentially a haptic motor 48 for providing haptic feedback to the wearer are placed on the conductive pad 40, thereby ensuring that the biometric sensors 32 and haptic motor 48 are positioned correctly and are connected to the electronic circuitry of the hard hat 10.

The conductive pad 40 is connected directly with the control unit 18 through a physical connector 29 that might use a plug and play connection mechanism. The physical connector 29 will identify which biometric sensors 32 are on the suspension band assembly 14 and send that information directly to the control unit 18. The physical connector 29 ensures data and power transmission from the biometric sensors 32 and the haptic motor 48 to the central control unit 18 and vice versa. The flow of data will then enable processing of the sensor data.

The sweat band 34 is designed to fully enclose the biometric sensors 32 and the haptic motor 48. The sweat band 34 also contains holes 36 at certain locations to allow for the biometric sensors 32 to produce accurate sensor readings from the wearer's forehead.

The fully assembled integrative band 46 is attached to the suspension band assembly 14 in the same way as the cover or sweat band 34 in FIG. 3 by placing the integrative band 46 over the suspension band assembly 14.

With setup described in either FIG. 3 or FIG. 4, the biometric sensor assembly 24 is built in a way that it can provide for a warning mechanism that alerts the wearer via a certain notification system. For example, in case the central control unit 18 processes the data of the biometric sensors 32 and identifies that the measured biometric data of the wearer deviates significantly from a previously defined threshold, an audio message could be played to the wearer through the speaker set 42 (as illustrated in FIG. 1). The wearer will therefore immediately receive a respective warning if one of his or her biometrics shows a significant deviation. An alternative to an audio signal could be that the warning signal is being visualized to the wearer through a signaling light indicator 50 that is included in the hard hat 10, or that the wearer receives haptic feedback through a haptic motor 48 that is attached to the suspension band assembly 14.

The invention has been described in an illustrative manner. It is to be understood that the terminology, which has been used, is intended to be in the nature of words of description rather than of limitation.

Many modifications and variations of the invention are possible in light of the above teachings. Therefore, within the scope of the appended claims, the invention may be practiced other than as specifically described.

We claim:

1. A biometric sensor assembly for measuring biometric data of a wearer of a hardhat, said biometric sensor assembly comprising:
   a suspension harness to be removably secured to the hardhat;
   a conductive pad removably secured to said suspension harness;
   a plurality of biometric sensors attached to said conductive pad in a way that allows direct or indirect contact with the wearer to enable measurement of the biometric data; and
   an electrical connection of said plurality of biometric sensors and the hardhat for data and power transmission.

2. A biometric sensor assembly as set forth in claim 1 including a feedback mechanism that provides feedback to user.

3. A biometric sensor assembly as set forth in claim 1 including a haptic motor fixedly secured to said conductive pad allowing direct or indirect contact with body of the wearer to provide feedback to the wearer.

4. A biometric sensor assembly as set forth in claim 1 including a cover removably covering said conductive pad, said plurality of biometric sensors, and a portion of said suspension harness.

5. A biometric sensor assembly as set forth in claim 4 wherein said cover includes a hole disposed adjacent a portion of said plurality of said biometric sensors to allow each of said plurality of biometric sensors requiring direct measurement to function and to measure the biometric data.

6. A biometric sensor assembly as set forth in claim 1 wherein said electrical connection is a plug and play connection.

* * * * *